United States Patent [19]
Burdette et al.

[11] Patent Number: 5,908,924
[45] Date of Patent: Jun. 1, 1999

[54] CLONING AND EXPRESSION OF THE GENE ENCODING THERMOANAEROBACTER ETHANOLICUS 39E SECONDARY-ALCOHOL DEHYDROGENASE AND ENZYME BIOCHEMICAL CHARACTERIZATION

[75] Inventors: Douglas S. Burdette, Monmouth Junction, N.J.; Joseph G. Zeikus, Okemos, Mich.

[73] Assignee: Michigan State University, Lansing, Mich.

[21] Appl. No.: 08/805,191

[22] Filed: Feb. 27, 1997

Related U.S. Application Data

[60] Provisional application No. 60/012,331, Feb. 27, 1996.

[51] Int. Cl.$^6$ .............................. C07H 21/04; C12N 9/04
[52] U.S. Cl. ........................................... 536/23.2; 435/190
[58] Field of Search ............................................. 536/23.2

[56] References Cited

PUBLICATIONS

Bryant, Frank O., et al., "Purification and Properties of Primary and Secondary Alcohol Dehygrogenases from *Thermoanaerobacter ethanolicus*," *Applied and Environmental Microbiology*, 54(2):460–465 (Feb. 1988).

Burdette, Douglas, et al., "Purification of acetaldehyde dehydrogenase and alcohol dehydrogenases from *Thermoanaerobacter ethanolicus* 39E and characterization of the secondary–alcohol dehydrogenase (2° Adh) as a bifunctional alcohol dehydrogenase—acetyl–CoA reductive thioesterase," *Biochem. J.*, 302:163–170 (1994).

Genbank Accession No. M84723, Complete coding sequence of C. beijerinckii NADP–Dependent alcohol dehydrogenase gene (1992).

Ismaiel, Adan A., et al., Purification and Characterization of a Primary–Secondary Alcohol Dehydrogenase from Two Strains of *Clostridium beijerinckii*, *Journal of Bacteriology*, 174(16):5097–5105 (Aug. 1993).

(List continued on next page.)

*Primary Examiner*—Rebecca E. Prouty
*Assistant Examiner*—Einar Stole
*Attorney, Agent, or Firm*—Quarles & Brady LLP

[57] ABSTRACT

The adhB gene encoding *Thermoanaerobacter ethanolicus* 39E secondary-alcohol dehydrogenase (2° Adh) was cloned, sequenced, and expressed in *Escherichia coli*. The 1056 bp gene encodes a homotetrameric recombinant enzyme consisting of 37.7 kDa subunits. The purified recombinant enzyme is optimally active above 90° C. with a half-life of approximately 1.7 h at 90° C. An NADP(H)-dependent enzyme, the recombinant 2° Adh has 1400-fold greater catalytic efficiency in propan-2-ol versus ethanol oxidation. The enzyme was inactivated by chemical modification using dithionitrobenzoate (DTNB) and diethylpyrocarbonate, indicating that Cys and His residues are involved in catalysis. Zinc was the only metal enhancing 2° Adh reactivation after DTNB modification, implicating the involvement of a strongly bound zinc in catalysis. Arrhenius plots for the oxidation of propan-2-ol by the native and recombinant 2° Adhs were linear from 25° C. to 90° C. when the enzymes were incubated at 55° C. prior to assay. Discontinuities in the Arrhenius plots for propan-2-ol and ethanol oxidations were observed, however, when the enzymes were preincubated at 0° C. or 25° C. The observed Arrhenius discontinuity, therefore, resulted from a temperature dependent, catalytically significant 2° Adh structural change. Hydrophobic Cluster Analysis comparisons of both mesophilic versus thermophilic 2° Adh and 1° versus 2° Adh amino acid sequences were performed. These comparisons predicted that specific proline residues may contribute to 2° Adh thermostability and thermophilicity, and that the catalytic Zn ligands are different in 1° Adhs (two Cys and a His) and 2° Adhs (Cys, His, and Asp).

2 Claims, 2 Drawing Sheets

OTHER PUBLICATIONS

Keinan, Ehud, et al., "Synthetic Applications of Alcohol-Dehydrogenase from *Thermoanaerobium brockii*," *Ann. N.Y. Acad. Sci.*, 501:130–149 (1987).

Lamed, Raphael J., et al., "Novel NADP–linked alcohol–aldehyde/ketone oxidoreductase in thermophilic ethanologenic bacteria," *Biochem. J.*, 195:183–190 (1981).

Lee, Young–Eok, et al., "Taxonomic Distinction of Saccharolytic Thermophilic Anaerobes: Desciption of *Thermoanaerobacterium xylanolyticum* gen. nov., sp. nov., and *Thermoanaerobacterium saccharolyticum* gen. nov., sp. nov.; Reclassification of *Thermoanaerobium brockii, Clostridium thermosulfurogenes,* and *Clostridium thermohydrosulfuricum* E100–69 as *Thermoanaerobacter brockii* comb. nov., *Thermoanaerobacterium thermohydrosulfurigenes* comb. nov., and *Thermoanaerobacter thermohydrosulfuricus* comb. nov., Respectively; and Transfer of *Closteridium Thermohydrosulfuricum* 39E to *Thermonanaerobacter ethanolicus,*" *International Journal of Systematic Bacteriology*, 43(1):41–51 (Jan. 1993).

Nagata, Yasu, et al., "NADP–linked alcohol dehyrdogenases from extreme thermophiles: Simple affinity purification schemes, and comparative properties of the enzymes from different strains," *Bioseparation*, 2:353–362 (1992).

Peretz, Moshe, et al., "Amino Acid Sequence of Alcohol Dehydrogenases from the Thermopilic Bacterium *Thermoanaerobium brockii,*" *Biochemistry*, 28:6549–6555 (1989).

Steinbuchel, Alexander, et al., "A multifunctional fermentative alcohol ehydrogenase *Alcaligenes eutrophus:* purification and properties," *European Journal of Biochemistry*, 141(3):555–564 (Feb. 1984).

Burdette et al. (1996) Cloning and expression of the gene encoding the *Thermoanaerobacter ethanolicus* 39E secondary–alcohol dehydrogenase and biochemical characterization of the enzyme. Biochemical Journal 316 (Part 1): 115–122, May 28, 1996.

FIG 1

FIG 2

CLONING AND EXPRESSION OF THE GENE ENCODING THERMOANAEROBACTER ETHANOLICUS 39E SECONDARY-ALCOHOL DEHYDROGENASE AND ENZYME BIOCHEMICAL CHARACTERIZATION

CROSS-REFERENCE TO RELATED APPLICATIONS

This application claims the benefit of U.S. Provisional Application No. 60/012,331, filed Feb. 27, 1996.

STATEMENT REGARDING FEDERALLY SPONSORED RESEARCH OR DEVELOPMENT

Not applicable.

ABBREVIATIONS USED IN THIS APPLICATION

In this application, the following abbreviations are used:

| | |
|---|---|
| Adh | alcohol dehydrogenase |
| 1° Adh | primary-alcohol dehydrogenase |
| 2° Adh | secondary-alcohol dehydrogenase |
| DTNB | dithionitrobenzoate |
| DEPC | diethylpyrocarbonate |
| HCA | Hydrophobic Cluster Analysis |
| DTT | dithiothreitol |
| MALDI | matrix associated laser desorption ionization mass spectrometry |
| EDTA | (ethylenedinitrilo) tetraacetic acid trisodium salt |
| ORF | open reading frame |
| RBS | ribosome binding site |

BACKGROUND OF THE INVENTION

The present invention relates to the cloning and expression of a gene encoding an enzyme. More particularly, it relates to the cloning and expression of a gene encoding an alcohol dehydrogenase.

Alcohol dehydrogenases (Adhs) (EC 1.1.1.1 [NADH] or EC 1.1.1.2 [NADPH]) are well studied as a structurally conserved class of enzyme [1]. The X-ray structure of the horse liver primary-alcohol dehydrogenase (1° Adh) is known, and the properties of this enzyme have been extensively detailed [1,2]. Adhs are typically dimeric or tetrameric pyridine dinucleotide-dependent metalloenzymes with a zinc atom involved in catalysis. Adh proteins have been classified as 1° or 2° Adhs based on their relative activities toward 1° and 2° alcohols. It generally has been assumed that 1° and 2° Adhs are structurally similar, and that their substrate differences are due to relatively small changes in their active site architecture. Tetrameric 2° Adhs have been reported from a number of microorganisms [3–7]. The *Thermoanaerobacter ethanolicus* 39E 2° Adh is a bifunctional Adh/acetylCoA reductive thioesterase [7]. It has been proposed to function physiologically by oxidizing nicotinamide cofactor during ethanol formation, indirectly preventing glycolytic inhibition at the glyceraldehyde dehydrogenase step [8].

2° Adhs are attractive subjects for use as catalysts of chiral chemical production because of their broad specificities and their highly enantiospecific conversion of prochiral ketones to alcohols [9–12]. Two issues facing the commercial scale application of 2° Adhs in chiral syntheses are the difficulty of regenerating and retaining expensive nicotinamide cofactor and the lack of inexpensive, highly stable enzymes. Cofactor regeneration and retention have been overcome by numerous strategies [13,14]. While thermophilic enzymes are generally much more stable than their mesophilic counterparts, the organisms that produce thermophilic 2° Adhs grow slowly and to low cell densities, making an alternative expression system for these enzymes crucial for both their commercial application and detailed protein structure-function studies.

The discovery of thermophilic bacteria has provided the opportunity to isolate thermostable enzymes directly. The thermophilic anaerobes *T. ethanolicus* and *Thermoanaerobacter brockii* [15] express extremely enantiospecific 2° Adhs that are stable above 70° C. These two 2° Adhs have been proposed to be extremely structurally similar based on similar molecular weight and kinetic characteristics [16]. While the *Clostridium beijerinckii* gene (adhB) encoding a mesophilic NADP(H)-dependent 2° Adh has been cloned and sequenced (Genbank, Acc. no. M84723), and while the amino acid sequence of the *T. brockii* 2° Adh has been determined by Edman degradation [17], no cloned thermophilic 2° Adh is available for detailed biochemical studies. The amino acid sequence of the *T. ethanolicus* 39E 2° Adh was not publically available before the priority date of this patent application.

BRIEF SUMMARY OF THE INVENTION

The present invention relates to the cloning, sequencing, and expression of the gene encoding the thermophilic *T. ethanolicus* 2° Adh. The kinetic and thermal properties of the recombinant enzyme are disclosed. The biochemical basis for enzyme discontinuous Arrhenius plots is described. Finally, the protein sequence information is used to examine the structural relationship between thermophilic and mesophilic 1° Adhs and 2° Adhs. These comparisons are used to predict the 2° Adh catalytic Zn liganding residues and the potential involvement of specific prolines in 2° Adh thermal stability.

DETAILED DESCRIPTION OF THE INVENTION

MATERIALS AND METHODS

Chemicals and reagents

All chemicals were of at least reagent/molecular biology grade. Gases were provided by AGA specialty gases (Cleveland, Ohio), and made anaerobic by passage through heated copper filings. Oligonucleotide syntheses and amino acid sequence analyses were performed by the Macromolecular Structure Facility (Department of Biochemistry, Michigan State University). The kanamycin resistance Gen-Block (EcoRI) DNA cartridge used in expression vector construction was purchased from Pharmacia (Uppsala, Sweden) [18].

Media and strains

*T. ethanolicus* 39E (ATCC #33223) was grown in TYE medium as previously described [19]. All batch cultures were grown anaerobically under an $N_2$ headspace. *Escherichia coli* DH5α containing the recombinant adhB gene was grown in rich complex medium (20 g $l^{-1}$ tryptone, 10 g $l^{-1}$ yeast extract, 5 g $l^{-1}$ NaCl) at 37° C. in the presence of 25 mg $ml^{-1}$ kanamycin and 100 mg $ml^{-1}$ ampicillin.

DNA manipulations and library construction

Plasmid DNA purification, restriction analysis, PCR, and colony and DNA hybridizations were performed using conventional techniques [20,21]. *T. ethanolicus* chromosomal DNA was purified as previously described [22]. Partially digested 2–5 kb Sau3A I fragments were isolated by size fractionation from a 10–40% sucrose gradient [20] and ligated into pUC18 BamH I/BAP (Pharmacia, Uppsala, Sweden). The ligation mixture was transformed into *E. coli* DH5α by electroporation [21]. Degenerate primers (1) (5'-ATGAA(R)GG(N)TT(H)GC(N)ATG(Y)T) and (2) (5'-G(W) (N)GTCATCAT(R)TC(N)G(K) (D)ATCAT) were used to synthesize the homologous probe for colony hybridization. The DNA fragment containing the adhB gene was sequenced using the method of Sanger et al. [24].

Enzyme purification

The native 2° Adh was purified by established techniques [7]. The recombinant enzyme was purified from *E. coli* DH5α aerobically. The pelleted cells from batch cultures were resuspended (0.5 g wet wt. $ml^{-1}$) in 50 mM Tris:HCl [pH 8.0] (buffer A) containing 5 mM DTT, and 10 mM $ZnCl_2$, and lysed by passage through a French pressure cell. The clarified lysate was incubated at 65° C. for 25 min and then centrifuged for 30 min at 15000 g. The supernatant was applied to a DEAE-sephacryl column (2.5 cm×15 cm) that was equilibrated with buffer A and eluted using a 250 ml NaCl gradient (0–300 mM). Active fractions were diluted 4-fold in buffer A and applied to a Q-sepharose column (2.5 cm×10 cm) equilibrated with buffer A. Purified enzyme was eluted using a 250 ml NaCl gradient (0–300 mM).

A more preferred purification method that yielded 2° ADH of >90% purity was as follows. The cells were resuspended in the above-noted buffer A with DTT and $ZnCl_2$ and were heated to 85° C. for 15 minutes. The cells were cooled on ice for 30 minutes and were then centrifuged for 30 minutes at 15,000×g. Ammonium sulfate was added to the supernatant to 50% (w:v) with stirring at 4° C. for 30 minutes. The supernatant was again subjected to centrifugation for 30 minutes at 15,000×g. The ammonium sulfate in the supernatant was increased to 70% (w:v) with stirring at 4° C. for 30 minutes. The supernatant was again subjected to centrifugation for 30 minutes at 15,000×g. The pellet was resuspended in the same buffer.

Molecular mass determination

Recombinant holoenzyme molecular mass was determined by comparison with protein standards (Sigma; St. Louis, Mo.) using gel filtration chromatography (0.5 ml $min^{-1}$) with a Pharmacia S300 column (110 cm×1.2 cm) equilibrated with buffer A containing 200 mM NaCl. Subunit molecular mass values were determined by matrix associated laser desorption ionization mass spectrometry (MALDI) at the Michigan State University Mass Spectrometry Facility.

Kinetics and thermal stability

The standard 2° Adh activity assay was defined as $NADP^+$ reduction coupled to propan-2-ol oxidation at 60° C. as previously described [7]. The enzyme was incubated at 55° C. for 15 min prior to activity determination unless otherwise indicated. Assays to determine $Km_{app}$ and $Vmax_{app}$ were conducted at 60° C. with substrate concentrations between $20 \times Km_{app}$ and $0.2 \times Km_{app}$. Kinetic parameters were calculated from nonlinear best fits of the data to the Michaelis-Menten equation using Kinzyme software [26]. Protein concentrations were measured using the bicinchoninic acid procedure (Pierce; Rockford, Ill.) [27].

2° Adh thermostability was measured as the residual activity after timed incubation at the desired temperatures. Thermal inactivation was stopped by incubation for 30 min at 25° C., and samples were prepared for activity assays by preincubation at 55° C. for 15 min. Incubations were performed in 100 ml PCR tubes (cat. #72.733.050, Sarstedt; Newton, N.C.) using 200 mg $ml^{-1}$ protein in 100 ml buffer A. Activity was determined using the unfractionated samples. The temperature effect on enzyme activity was studied using the substrates propan-2-ol or ethanol at $10 \times Km_{app}$ concentrations.

To study the effect of enzyme preincubation temperature on enzyme reaction rates, the 2° Adh was incubated at 0° C., 25° C., or 55° C. for 15 min prior to activity determinations in the temperature range 30–90° C. Tris-HCl buffer pH values were adjusted at 25° C. to be pH 8.0 at the temperature they were used (thermal correction factor=−0.031 $\Delta$pH $°C.^{-1}$). The statistical significance of the differences between the Arrhenius plot slopes above and below the discontinuity temperatures was determined by covariance analysis [25].

Chemical modification

Cysteine residues were reversibly modified using dithionitrobenzoate (DTNB) at 25° C. and 60° C. [28]. DTNB-inactivated 2° Adh was reactivated using DTT in the presence of 0.01 mM to 1.0 mM metal salts or 0.5 mM to 3.0 mM EDTA. Histidine residues were chemically modified with diethylpyrocarbonate (DEPC) by incubation with 20 mM or 40 mM DEPC in 50 mM phosphate buffer (pH 6.0) at 25° C. for 1.0 h and the reaction was quenched by addition of 0.5×volume of 0.5 M imidazole (pH 6.5) [29].

Protein sequence comparisons

The peptide sequences of the *Bacillus stearothermophilus* (acc. #D90421), *Sulfolobus solfataricus* (acc. #S51211), and *Zymomonas mobilis* (acc. #M32100) 1° Adhs and of the *Alcaligenes eutrophus* (acc. #J03362) and *Clostridium beijerinckii* (acc. #M84723) 2° Adhs were obtained from GenBank. The horse liver 1° Adh [1] and the *T. brockii* 2° Adh [17] peptide sequences were obtained from the literature. Access to GenBank, standard sequence alignments, and percentages of amino acid similarity/identity were performed using the Program Manual for the Wisconsin Package, Version 8, September 1994 (Genetics Computer Group; Madison, Wis.). Protein sequence alignments were performed using Hydrophobic cluster analysis (HCA) [30]. HCA plots of individual protein sequences were generated using HCA-Plot V2 computer software (Doriane; Le Chesnay, France).

Nucleotide sequence accession number

The GenBank accession number for the sequence disclosed herein is #U49975.

RESULTS

Cloning and sequencing of the T. ethanolicus adhB gene

Figure 1:
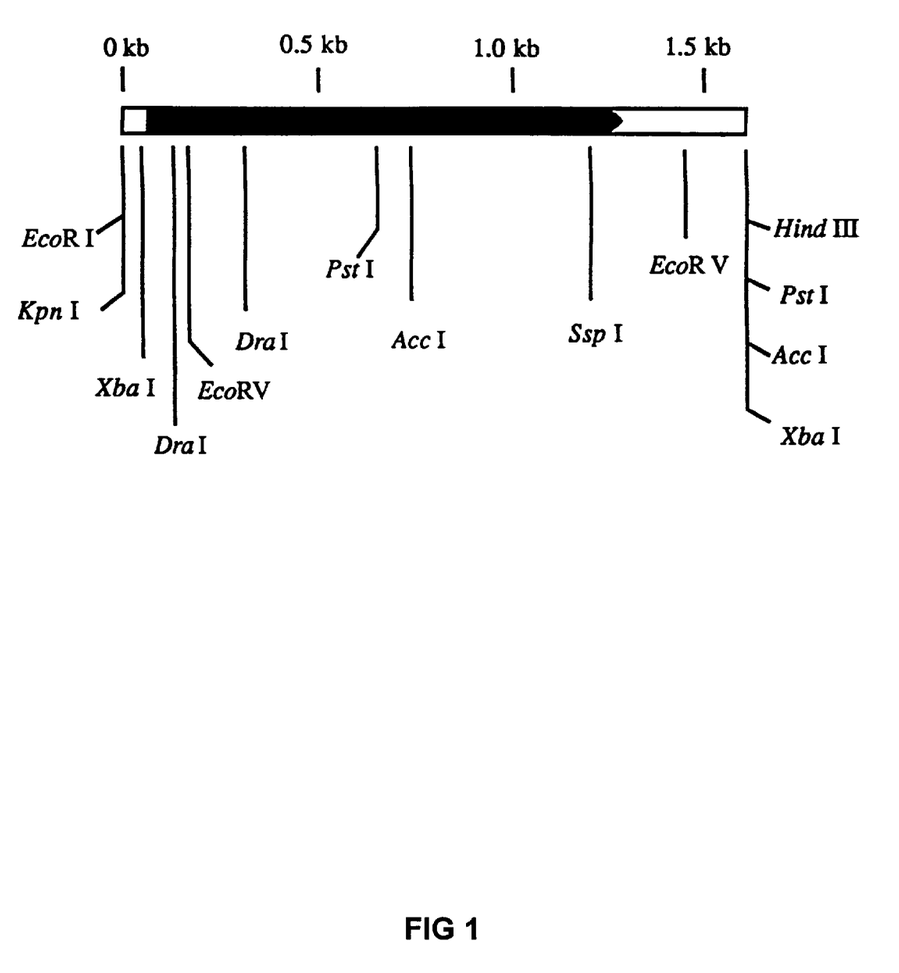
FIG. 1. Restriction map of the *T. ethanolicus* 39E 2° Adh clone (R35A25). The flanking restriction sites are from the plasmid polylinker. The adhB gene coding region begins downstream of the XbaI site and terminates past the SspI site.

The *T. ethanolicus* 2° Adh was cloned from a *T. ethanolicus* chromosomal DNA library by homologous hybridization. The N-terminal sequence of the native *T. ethanolicus* 2° Adh was determined (MKGFAML) and was identical to those of *C. beijerinckii* and *T. brockii* 2° Adhs. This sequence was used to generate primer (1). Alignment of the *C. beijerinckii* and *T. brockii* 2° Adh peptide sequences indicated another conserved region (residues 147–153) that would reverse translate into a low-degeneracy oligonucleotide (primer [2]). A 470 bp PCR product was obtained using primers (1) and (2), and using *T. ethanolicus* chromosomal DNA as the template, as expected from the position of primers (1) and (2) in the *C. Beijerinckii* and *T. brockii* 2° Adhs. This PCR product was used as a homologous probe to screen the *T. ethanolicus* genomic library. The positive clone showing the highest 2° Adh activity at 60° C. was selected for further studies. Plasmid pADHB25-C contained a 1.6 kb Sau3A I insert and was shown by subsequent sequencing and peptide analyses to carry the complete adhB gene. The 1.6 kb insert was subcloned into the pBluescriptIIKS(+) Xba I site to construct the expression plasmid pADHB25. The physical map of the pADHB25 insert that includes the native *T. ethanolicus* 39E transcriptional and translational signal sequences is shown in FIG. 1. Plasmid pADHB25 was stabilized by insertion of a kanamycin resistance cartridge into the vector EcoRI site, allowing dual selection on kanamycin and ampicillin. From the pADHB25-kan construct, the 2° ADH coding region was cloned after PCR amplification. The PCR primers used were 5'-CGGGGTACCCCGTATTTTAGGAGGTGTTTAA-3' (5'-end) (SEQ ID NO:6) and 5'-CAGTCCGGGCCCTTATGCTAATATTACAACAGGTT TG-3' (3'-end) (SEQ ID NO:7). The 5'-end primer introduces a KpnI site. The 3'-end primer introduces an ApaI site. A KpnI/ApaI fragment containing the identical coding region, but lacking the native transcriptional and translational signal sequences and the downstream ORF, was obtained from the amplified product and was cloned into Bluescript IIKS+ vector so that the start codon of the 2° ADH gene was 81 bases from the Lac promoter. The coding region began with two consecutive ATG (Met) codons. This clone was called pADHBKA4-kan. It is noted that a protein having two Met residues at its N-terminus is kinetically indistinguishable from an otherwise identical protein having only one Met residue.

The nucleotide sequence of the pADHB25 insert is attached as SEQ ID NO: 1. A unique open reading frame (ORF) was identified that encoded a polypeptide which was highly homologous to *C. beijerinckii* 2° Adh, and which started with the N-terminal sequence of the native *T. ethanolicus* 2° Adh. Two consecutive ATG codons (a "strong start") were identified as potential translation initiation codons. The N-terminus of the native 2° Adh protein starts with a single Met, suggesting that the first ATG codon is not translated or is post-translationally removed. A potential ribosome binding site (RBS) (positions 223–228) is located 10 bp upstream of the start codon. A potential transcriptional promoter was identified approximately 70–100 bp upstream of the RBS. The "−35" and "−10" regions are highly similar to the *E. coli* consensus promoter sequences [31], and are separated by 16 bp. The "−10" region is duplicated with the second copy overlapping the first. Because of its improper distance from the "−35" region, this second copy may only provide an A+T rich sequence to aid in strand separation. The *T. ethanolicus* 39E gene can be characterized as comprising at least 60%, preferably between 60% and 70%, A-T pairs in its coding sequence. No transcriptional stop site was identified downstream of adhB. In this region, instead, a truncated ORF, preceded by an RBS, was identified. It translated into a 45 amino acid peptide fragment (SEQ ID NO: 3) 46% identical and 68% similar to the product of a similar truncated ORF located downstream of *C. beijerinckii* adhB gene. Insufficient similarity to other sequences in GenBank was found, so the function of this ORF remains unknown, although the sequence encoding the ORF can be used as a probe for the chromosomal region of adhB or adjacent DNA regions.

Sequence comparison of 1° and 2° Adhs

Standard alignments of 1° and 2° Adh amino acid sequences indicated a high level of similarity among the three 2° Adhs from obligate anaerobes (Table 1). The *T. ethanolicus* 2° Adh (SEQ ID NO: 2) differed from the *T. brockii* enzyme (Genbank X1771790) by only three residues (amino acid residues 91, 313, and 325 of SEQ ID NO: 1), and was 75% identical to the enzyme from the mesophile *C. beijerinckii* (Genbank X64841). The similarity was lower for comparisons with the 2° Adh from the obligate aerobe *A. eutrophus*. The 1° Adhs showed less sequence conservation (25 to 54% identity and 49 to 71% similarity) than the 2° Adhs, and showed only 20 to 27% identity (and 48 to 51% similarity) to the 2° Adhs. Based on these standard alignments, the conservation of important core domain residues, amino acids lining the active site pocket, and structurally conserved glycines identified for the horse liver enzyme [1] was higher among all the peptides.

HCA comparisons allow the alignment of potentially similar 2° or 3° structural regions between enzymes with dissimilar amino acid sequences. The Rossmann fold consensus sequences {Gly-Xaa-Gly-Xaa-Xaa-Gly-(Xaa)$_{18-20}$ [negatively charged amino acid for NAD(H) dependent or neutral amino acid for NAD(P)(H)]} [32] identified in each of the Adh peptides were used to direct HCA alignments of 1° and 2° Adh peptides. The consensus motifs of the NADP(H) linked *T. ethanolicus* and *C. beijerinckii* 2° Adhs were identified as Gly$^{174}$-Xaa-Gly$^{176}$-Xaa-Xaa-Gly$^{179}$, Gly$^{198}$, and those of the NAD(H) dependent *B. stearothermophilus* and horse liver 1° Adh were identified as Gly$^{172}$-Xaa-Gly$^{174}$-Xaa-Xaa-Gly$^{177}$, Asp$^{195}$ and Gly$^{199}$-Xaa-Gly$^{201}$-Xaa-Xaa-Gly$^{204}$, Asp$^{223}$, respectively. This alignment also predicts 71 to 94% overall similarity between 1° and 2° Adhs for the critical hydrophobic core residues (71 to 94%), active site pocket residues (71 to 100%), and structurally critical glycines (100% in all cases) identified in the horse liver enzyme.

The HCA comparison allowed the identification of corresponding cluster regions and catalytically important residues in all four dehydrogenases based on the corresponding residues identified for the horse liver enzyme [1,2]. The horse liver 1° Adh contains two Zn atoms per subunit, one structural and one catalytic [1]. The thermophilic *B. stearothermophilus* 1° Adh contained a region involving cysteine residues 97, 100, 103, and 111 that is analogous to the structural Zn binding loop in the horse liver Adh (involving Cys$^{92}$, Cys$^{95}$, Cys$^{98}$, and Cys$^{106}$). However, no analogous structural Zn binding loop regions were identified in the *T. ethanolicus* and *C. beijerinckii* 2° Adhs. The catalytic Zn ligands in the horse liver enzyme have been established (Cys$^{46}$, His$^{68}$, and Cys$^{174}$). The N-terminal cysteine and histidine ligands to the catalytic Zn atom appear to be conserved in both the 1° and 2° Adh sequences. However, the second cysteine ligand in the horse liver 1° Adh (Cys$^{174}$), conserved in the *B. stearothermophilus* 1° Adh(Cys$^{148}$), is substituted with an aspartate residue (Asp$^{150}$) in both the *T. ethanolicus* and *C. beijerinckii* proteins. The *A. eutrophus* and *T. brockii* 2° Adhs also conserved corresponding aspartate residues and appeared to lack 1° Adh-like structural Zn binding loops.

Sequence comparison of 2° Adh enzymes from a mesophile and thermophiles

The structural constraints introduced by proline residues have been proposed as a mechanism involved in protein thermostabilization [33]. Among the twelve nonconservative sequence substitutions between the mesophilic *C. beijerinckii* 2° Adh and the thermophilic *T. ethanolicus* 2° Adh, nine correspond to the introduction of prolines (22, 24, 149, 177, 222, 275, 313, 316, and 347) in the *T. ethanolicus* protein. All but Pro$^{313}$ are also present in the thermophilic *T. brockii* 2° Adh. The mesophilic 2° Adh subunit contained a total of 13 prolines (3.7%) while the *T. ethanolicus* and *T. brockii* subunits contained 22 prolines (6.2%) and 21 prolines (6.0%), respectively. Prolines 20, 22, and 24 are in a 9 residue stretch of hydrophilic amino acids near the putative catalytic Zn ligand Cys$^{37}$. Pro$^{149}$ interrupts a hydrophobic cluster and is next to another putative Zn ligand, Asp$^{150}$. The nicotinamide cofactor binding motif includes Pro$^{177}$ which also interrupts a hydrophobic cluster region. Prolines 222, 275, 313, 316, and 347 are located in short (two to four residue) hydrophilic stretches that form putative turn regions.

In this patent application, a mesophilic bacterium is characterized as having optimal growth between 25° C. and 45° C., while a thermophilic bacterium, on the other hand, has optimal growth between 45° C. and 80° C. See Vieille, C. et al., *Biotechnology Annual Review*, 2:1–83 (1996). *T. ethanolicus* 39E 2° Adh is both more thermostable and thermophilic than *T. beijerinckii* 2° Adh or *T. brockii* 2° Adh. Thermostability is a measure of the time for which enzyme can be heated to a certain temperature (e.g. 85° C.) with recovery of full enzyme activity. Thermophilicity is a measure, in units, of an enzyme's activity at a selected elevated temperature.

*T. ethanolicus* 39E 2° Adh retains 100% activity after incubation for more than one hour at 90° C., while *T. brockii* 2° Adh retains only 40% activity after incubation for 30 minutes at 91° C. *C. beijerinckii* was completely inactivated within 10 minutes at 70° C. [6]. The improved thermostability and thermophilicity make the *T. ethanolicus* 39E 2° Adh enzyme a superior choice for process design, offering longer catalyst life and, therefore, lower cost. Because of its stability, the protein can also be easily immobilized for use in combinatorial chemistry processes. The protein can also be linked to redox dyes or can be used as an immunological carrier.

Purification and characterization of the recombinant 2° Adh

The recombinant *T. ethanolicus* 2° Adh was highly expressed in *E. coli* in the absence of induction and no significant increase was seen upon induction with 5.0 mM isopropylthio-β-D-galactoside. A preferred expressible construct (pADHBKA4-kan) that encoded the cloned 2° Adh gene did not include the native transcription and translation directing sequences. Instead, the coding sequence was placed 81 bases downstream of the Lac promoter. Expression as high as 15% of total protein was observed from this construct. The enzyme expression level from pADHB25, a less preferred construct, was similar in *E. coli* and in the native organism (1% to 5% of total protein). The recombinant enzyme was purified 36-fold to homogeneity (as determined by the presence of a single band on SDS-PAGE). The subunit molecular masses were calculated from the average of 3 (native enzyme) and 5 (recombinant enzyme) determinations using MALDI, yielding masses for the native and recombinant enzyme subunits of 37707 Da and 37854 Da, respectively. These values are within the generally accepted error of the technique (~1%), and are in agreement with the theoretical molecular mass for the native enzyme based on the gene sequence (37644 Da). N-terminal amino acid analysis of the recombinant enzyme indicated that in 72±5% of the recombinant protein the two N-terminal ATG codons had been translated, while 28±2% of the protein contained a single N-terminal Met residue, like the native enzyme. The increased mass of 147 Da determined for the recombinant enzyme is consistent with the mass of one Met residue (149.2 Da), although this difference is small compared to the measurement error associated with MALDI. The recombinant holoprotein molecular mass was determined to be 160 kDa by gel filtration chromatography demonstrating that the recombinant *T. ethanolicus* 2° Adh, as the native enzyme, is a homotetramer.

The 2° Adh was completely inactivated at both 25° C. and 60° C. by cysteine-specific DTNB modification. Inactivation was reversed at 60° C. by the addition of DTT allowing the recovery of 34% initial activity (initial activity=54±3.0 U mg$^{-1}$). The addition of $CdSO_4$, $FeCl_2$, $MnCl_2$, $CaCl_2$, $MgCl_2$, NaCl (0.01 mM to 1.0 mM), or EDTA (0.5 mM to 3.0 mM) did not affect enzyme reactivation by DTT, and the addition of $CoCl_2$ or $NiCl_2$ reduced the recovered activity to only 10% or 15% of the initial activity, respectively. Zinc was the only metal to enhance the reactivation (up to 48% activity recovery in the presence of 100 mM $ZnCl_2$). DEPC modification of histidine residues also completely inactivated the enzyme.

Characterization of thermal and kinetic properties of the recombinant *T. ethanolicus* 2° Adh The activity of the recombinant 2° Adh toward Adh substrates was characterized. The $Vmax_{app}$ for propan-2-ol (47 U mg$^{-1}$) was 5-fold higher than for ethanol (10 U mg$^{-1}$), and the $Km_{app}$ toward the 1° alcohol (47 mM) was almost 43-fold higher than for the 2° alcohol (1.1 mM). The catalytic efficiency of the recombinant enzyme was determined to be approximately 200-fold greater toward the 2° alcohol (0.29 ml min$^{-1}$ mg$^{-1}$) than toward the 1° alcohol (0.00021 ml min$^{-1}$ mg$^{-1}$). The $Km_{app}$ for NADP$^+$ was 0.011 mM, and no NAD(H) dependent activity was detected.

Figure 2:
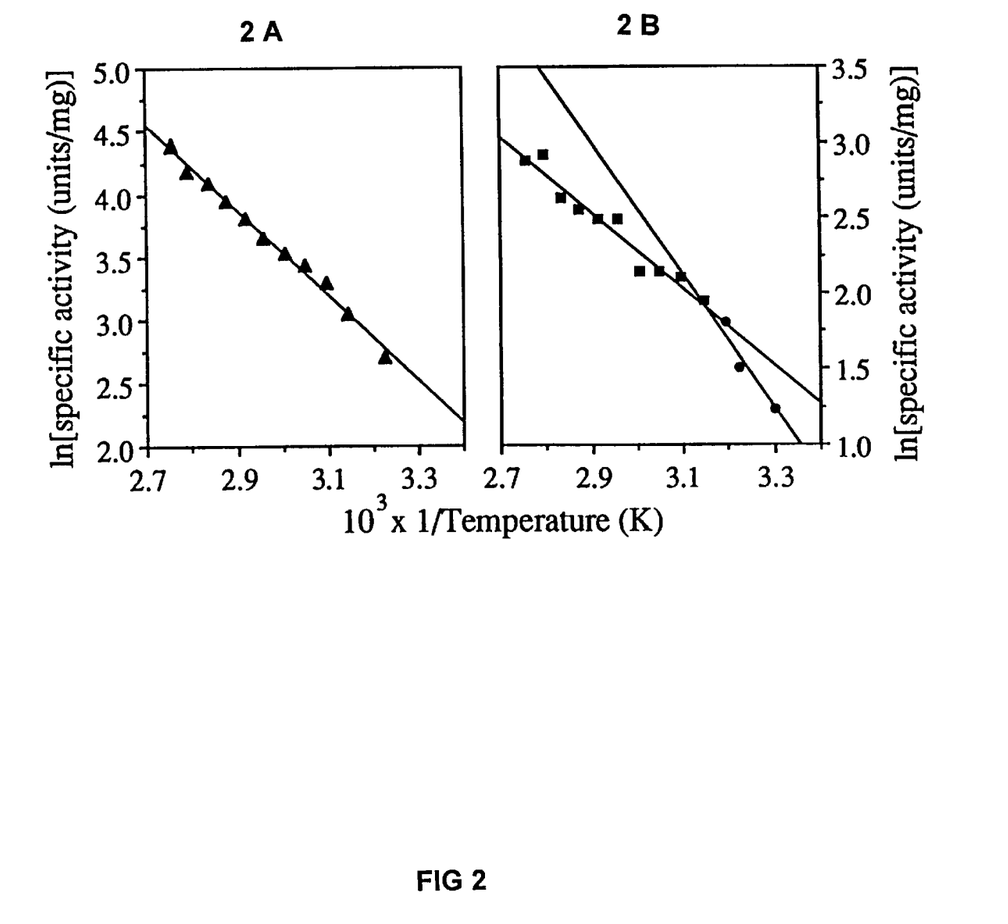
FIG. 2. Arrhenius plots for the recombinant *T. ethanolicus* 39E 2° Adh (A) Temperature-activity data for propan-2-ol oxidation between 25° C. and 90° C. with recombinant enzyme preincubated at 55° C. Linear regression best fit to the data was determined to be $y=13.674-3.3694 \times (R^2=0.993)$. (B) Temperature-activity data for ethanol oxidation between 25° C. and 90° C. with recombinant 2° Adh preincubated at 55° C. indicating points above (■) and below (●) the rate discontinuity. Linear regression best fits to the data were determined to be $y=9.7929-2.5036 \times (R^2=0.946)$ for points above and $y=15.730-4.3899 \times (R^2=0.969)$ for points below the discontinuity.

The temperature dependence of native and recombinant enzyme activities were determined to be similar. Thus, only the data obtained with the recombinant enzyme are reported here. *T. ethanolicus* 2° Adh activity was detected below 25° C. and increased to beyond 90° C. (FIG. 2A). The 2° Adh half-life at 90° C. was 1.7 h. The Arrhenius plot for the oxidation of propan-2-ol was linear from 25° C. to 90° C. when the enzyme was incubated at 55° C. prior to assay. Under the same conditions, however, a distinct discontinuity was seen in the Arrhenius plot for ethanol oxidation (FIG. 2B). Discontinuities were also observed at ~55° C. and ~46° C. for propan-2-ol and ethanol oxidations, respectively, when the enzyme was preincubated at 0° C. or 25° C. (Table 2). The slopes of the best fit regression lines above and below the discontinuity were significantly different beyond the 95% confidence level except for propan-2-ol oxidation by enzyme preincubated at 55° C., where the regression line slopes were similar at the 95% confidence level. The activation energies for propan-2-ol and ethanol oxidations were similar at assay temperatures above the discontinuities but were 15 to 20 kJ mol$^{-1}$ higher for ethanol oxidation than for propan-2-ol oxidation at temperatures below the discontinuity temperatures (Table 2). Furthermore, the differences between activation energies above and below the discontinuity temperatures (Δ) decreased with increasing preincubation temperatures. and the differences for ethanol oxidation were at least 3-fold higher than for propan-2-ol oxidation.

The following is a description of the evidence of the molecular bases for enzyme activity, thermophilicity, and discontinuous Arrhenius plots. Protein sequence comparisons predict that 1° and 2° Adhs have some structure-function similarities related to catalytic Zn and nicotinamide cofactor binding. However, differences in the hydrophobic clusters present in the overall 1° and 2° Adh sequences predict significant differences in the overall structures of these enzymes. The recombinant T. ethanolicus protein, with kinetic properties similar to those of the native enzyme [6], is a thermophilic and thermostable NADP(H) dependent enzyme that exhibits significantly greater catalytic efficiency toward 2° alcohols than 1° alcohols due to both lower $Km_{app}$ and higher $Vmax_{app}$ values. Chemical modification experiments suggest that enzyme activity requires at least Cys and His residues and a tightly bound Zn atom. Finally, the magnitude of the bend in the Arrhenius plots varied inversely with enzyme preincubation temperature, indicating the existence of a catalytically significant, temperature dependent structural change in the enzyme.

The adhB gene encoding the thermophilic T. ethanolicus 2° Adh was cloned by hybridization and expressed in E. coli. Comparisons of the native and recombinant enzyme N-terminal sequences and molecular masses showed that the recombinant enzyme differed from the native protein only by the addition of an N-terminal methionine. While the first ATG is the main translation start codon in E. coli, it is unknown if it is the sole initiation codon (and the first methionine is processed later), or if the second ATG is also used as an initiation codon. The presence of a truncated ORF (preceded by an RBS) 180 nucleotides downstream of adhB and the absence of any potential transcriptional stop signal suggested that adhB may be the first gene of an operon. The similarity between the truncated ORF reported here and the one downstream of C. beijerinckii adhB lends further support to this hypothesis.

HCA alignments of the 1° and 2° Adhs directed by their pyridine dinucleotide binding motifs indicated some structural similarity between these classes of enzymes. The negatively charged $Asp^{(223, 195, 215)}$ residues are consistent with the NAD(H) dependence of the horse liver, B. stearothermophilus, and A. eutrophus enzymes, respectively, while the presence of an uncharged residue ($Gly^{198}$) at the analogous position in the T. ethanolicus, T. brockii and C. beijerinckii 2° Adhs is consistent with the NADP(H) dependence of these enzymes [3,6,7]. Furthermore, residues identified in the enzyme hydrophobic core, residues lining the active site cavity, and structurally important glycines previously identified in the horse liver 1° Adh [1], were better conserved between proteins in this alignment than the overall peptide sequences. Similarity of putative structurally critical regions has been reported for other Adh comparisons [34]. The correlation between enzyme structure-function properties and the predictions of this alignment support its use in further Adh structure-function studies. However, the apparent lack of a structural Zn binding loop in the 2° Adhs, the reports of only tetrameric 2° Adhs but both tetrameric and dimeric 1° Adhs, and the significantly greater similarity between the 2° Adhs than between the 1° and 2° Adhs predicted by HCA comparison also suggests that, while functionally similar, 1° and 2° Adhs may be less structurally similar than was it previously believed.

The thermophilic T. ethanolicus 39E 2° Adh incubated at 90° C. retained detectable activity for more than one hour while the mesophilic C. beijerinckii 2° Adh was completely inactivated within 10 min at 70° C. [6]. Still, these two enzymes shared more than 85% sequence similarity. Nine of the nonconservative substitutions between the subunits of these proteins correspond to prolines in the T. ethanolicus enzyme. The similarly thermophilic T. brockii 2° Adh contains 8 of these additional prolines. This difference in proline content of the thermophilic versus mesophilic 2° Adhs is consistent with the hypothesis of Matthews et al. regarding the role of prolines in protein stabilization [33] and with the observations by numerous investigators of protein stabilization due to proline insertion [35,36], constrained loop regions [37], and proline substitution into loops [38–40]. The substituted prolines in the T. ethanolicus 2° Adh were either in short putative loop regions or in longer putative loop regions containing multiple prolines, suggesting that the specific placement as well as the number of prolines may be critical to their stabilizing effect. The difference in proline content between the T. ethanolicus and C. beijerinckii enzymes and their overall high sequence similarity makes these 2° Adhs an excellent system for testing the effect of proline insertion on protein structure stabilization.

Comparative sequence analysis predicted the involvement of specific Cys, His, and Asp residues in 2° Adh catalysis. Chemical modification of the recombinant and native T. ethanolicus 2° Adhs with DTNB established the importance of cysteine residues in catalysis. The observation that Zn was the only metal enhancing the enzyme reactivation after DTNB modification suggested that the enzyme is Zn dependent. This finding is in agreement with the previous report that, once inactivated by the sulfhydryl modifying reagent p-chloromercuribenzoate, the T. brockii 2° Adh recovered activity only in the presence of $ZnCl_2$ [3]. Here, the recovery of 34% initial activity upon reversal of DTNB modification in the absence of added metal and the inability of EDTA to reduce the rate of reactivation, even at 60° C., suggested that the catalytic metal remained tightly bound to the protein. Histidine specific modification of the T. ethanolicus enzyme by DEPC was also accompanied by complete enzyme inactivation, implicating a histidine residue in catalysis. The apparent lack of a structural Zn binding region in the 2° Adh subunits argues that the DTNB linked inactivation and Zn dependent reactivation are not due to the loss and recovery of a cysteine-liganded structural Zn. Therefore, the catalytically important cysteine and histidine residues may act as ligands to the catalytic Zn as described for other Adhs [1]. Determination of the importance of $Asp^{150}$ to 2° Adh activity awaits mutagenic, crystallographic, or physical biochemical analysis.

The temperature dependence of catalytic activities for the native and recombinant enzymes were similar. The Arrhenius plot for propan-2-ol oxidation by T. ethanolicus 2° Adh preincubated at 55° C. was linear, unlike that previously reported for the T. brockii 2° Adh [3]. However, statistically significant discontinuities in the Arrhenius plots for both ethanol and propan-2-ol oxidation by the T. ethanolicus enzyme were seen when the enzyme was preincubated at lower temperatures. A change in the rate determining step of the overall reaction and other explanations that do not invoke alterations in catalyst structure predict Arrhenius plot discontinuities [44,45]. A shift in the reaction slow step not related to an alteration in enzyme structure would be independent of the initial temperature of the enzyme, and is inconsistent with the inverse relationship observed here between enzyme preincubation temperature and the difference in activation energies above and below the discontinuity (D). At assay temperatures above the discontinuity, the reaction activation energies were similar for enzymes preincubated at 0° C., 25° C. and 55° C., unlike those at lower assay temperatures. This observation is consistent with the enzyme attaining its optimally active conformation rapidly enough at higher assay temperatures not to affect the measured rate. The discontinuity temperatures, being below the lowest reported temperatures for *T. ethanolicus* growth, are physiologically irrelevant, but they underscore the importance of treating thermophilic enzymes differently from mesophilic enzymes when conducting kinetic analyses. Furthermore, the differences between the low temperature activation energies for ethanol and propan-2-ol argue that substrate/product-protein interactions are important to the rate determining step in catalysis.

The Arrhenius plot was linear for propan-2-ol oxidation by the 2° Adh preincubated at 55° C., arguing that under these conditions the temperature dependence of reaction rate is due predominantly to the change in average substrate molecular energy rather than to a functionally significant structural change. Although these data are not conclusive, the lack of a catalytically significant alteration in enzyme structure, seen as an Arrhenius plot discontinuity, makes excessive rigidity (resistance to structural change) of the thermophilic protein unnecessary to explain the low *T. ethanolicus* 2° Adh activity at mesophilic temperatures compared to the activity of the mesophilic enzyme [6]. Therefore, while the *T. ethanolicus* 2° Adh can undergo a temperature dependent, catalytically significant structural change, an Arrhenius plot discontinuity cannot be invoked as evidence for greater thermophilic protein rigidity.

The linear Arrhenius plot for propan-2-ol oxidation by *T. ethanolicus* 2° Adh preincubated at 55° C. indicates that the low mesophilic temperature activity of this enzyme may be explained by the substrate energy alone. Arrhenius theory predicts increasing $Km_{app}$ and $Vmax_{app}$ with increasing temperature [44], and this effect has been confirmed for the *Thermotoga neopolitana* D-xylose isomerase [46]. The thermophilic 2° Adh has lower $Vmax_{app}$ values than would be predicted from extension of the mesophilic enzyme activity at 25° C. In fact, at 60° C. the thermophilic 2° Adh maintains $Km_{app}$ and $Vmax_{app}$ values toward substrates similar to those reported for the mesophilic enzyme at 25° C. These similar kinetic values suggest that the thermophilic enzyme channels more excess substrate binding energy into substrate binding and less into turnover [47]. Therefore, the *T. ethanolicus* 2° Adh appears to maintain substrate affinity at high temperatures by sacrificing high turnover number.

REFERENCES (ALL INCORPORATED HEREIN BY REFERENCE)

1. Brändén, C. -I., Jörnvall, H., Eklund, H. and Furugren, B. (1975) in The enzymes, vol. XI part A (Boyer, P. D., ed.), pp. 103–190, Academic Press, N.Y.
2. Eklund, H., Nordström, B., Zeppezauer, E., Söderlund, G., Ohlsson, I., Boiwe, T. and Brändén, C. -I. (1974) FEBS Lett. 44, 200–204
3. Lamed, R. J. and Zeikus, J. G. (1981) Biochem. J. 195, 183–190
4. Steinbüchel, A. and Schlegel, H. G. (1984) Eur. J. Biochem. 141, 555–564
5. Bryant, F. O., Wiegel, J. and Ljungdahl, L. (1988) Appl. Env. Microbiol. 54, 460–465
6. Ismaiel, A. A., Zhu, C. -X., Colby, G. D. and Chen, J. -S. (1993) J. Bacteriol. 175, 5097–5105
7. Burdette, D. S. and Zeikus, J. G. (1994) Biochem. J. 302, 163–170
8. Lovitt, R. W., Shen, G. -S. and Zeikus, J. G. (1988) J. Bacteriol. 170, 2809–2815
9. Keinan, E., Hafeli, E. K., Seth, K. K. and Lamed, R. L. (1986) J. Am. Chem. Soc. 108, 162–169
10. Keinan, E., Hafeli, E. K., Seth, K. K. and Lamed, R. L. (1986) Ann. N. Y. Acad. Sci. 501, 130–149
11. Hummel, W. (1990) Appl. Microbiol. Biotech. 34, 15–19
12. Keinan, E., Seth, K. K., Lamed, R. L., Ghirlando, R. and Singh, S. P. (1990) Biocatalysis 4, 1–15
13. Hummel, W. and Kula, M. -R. (1989) Eur. J. Biochem. 184, 1–13
14. Persson, M., Månsson, M. -O., Bülow, L. and Mosbach, K. (1991) Biotechnology 9, 280–284
15. Lee, Y. -E., Jain, M. K., Lee, C., Lowe, S. E., and Zeikus, J. G. (1993) Int. J. Syst. Bacteriol. 43, 41–51
16. Nagata, N., Maeda, K. and Scopes, R. K. (1992) Bioseparation 2, 353–362
17. Peretz, M. and Burstein, Y. (1989) Biochemistry 28, 6549–6555
18. Oka, A., Sugisaki, H. and Takanami., M. (1981) J. Mol. Biol. 147, 217–226
19. Zeikus, J. G., Hegge, P. W. and Anderson, M. A. (1979) Arch. Microbiol. 122, 41–48
20. Sambrook, J., Fritsch, E. F. and Maniatis, T. (1989) Molecular cloning: A laboratory manual $2^{nd}$ edition. (Nolan, C., ed.), Cold spring Harbor Press, N.Y.
21. Ausubel, F. M., Brent, R., Kingston, R. E., Moore, D. D., Seidman, J. G., Smith, J. A. and Struhl, K. (1993) Current Protocols in Molecular Biology (Janssen, K., ed.), Current Protocols, N.Y.
22. Doi, R. H. (1983) in Recombinant DNA Techniques: An Introduction (Rodriguez, R. L, and Tait, R. C., eds.), pp. 162–163, Benjamin-Cummings, CA
23. Lee., C. C., Wu, X., Gibbs, R. A., Cook, R. G., Muzny, D. M. and Caskey, C. T. (1988) Science 239, 1288–1291
24. Sanger, F., Nicklen, S. and Coulson, A. R. (1977) Proc. Natl. Acad. Sci. USA 74, 5463–5467
25. Remington, R. D. and Schork, M. A. (1985) in Statistics with applications to the biological and health sciences, pp. 296–309, Prentice-Hall, N.J.
26. Brooks, S. (1992) Biotechniques 13, 906–911
27. Smith, P. K., Krohn, R. I., Hermanson, G. T., Mallia, A. K., Gartner, F. H., Provenzano, M. D., Fugimoto, E. K., Goele, N. M., Olson, B. J. and Klenk, D. C. (1985) Anal. Biochem. 150, 76–85
28. Habeeb, A. F. S. A. (1972) in Methods in enzymology vol. 25: Enzyme structure, part B (Hirs, C. H. W. and Timasheff, S. N., ed.), pp. 457–459, Academic press, N.Y.
29. Miles, E. W. (1977) in Methods in enzymology vol. 47 (Hirs, C. H. W. and Timasheff, S. N., ed.), pp. 431–442, Academic press, N.Y.
30. Lemesle-Verloot, L., Henrissat, B., Gaboriaud, C., Bissery, V., Morgat, A. and Mornon, J. P. (1990) Biochimie 72, 555–574
31. Hawley, D. K. and McClure, W. R. (1983) Nucl. Acids Res. 11, 2237–2255
32. Wierenga, R. K. and Hol, G. J. (1983) Nature 302, 842–844
33. Matthews, B. W., Nicholson, H. and Becktel, W. (1987) Proc. Natl. Acad. Sci. USA 84, 6663–6667
34. Jendrossek, D., Steinbuechel, A. and Schlegel, H. G. (1988) J. Bacteriol. 170, 5248–5256
35. Herning, T., Katsuhide, Y., Taniyama, Y. and Kikuchi, M. (1991) Biochemistry 30, 9882–9891

36. Herning, T., Katsuhide, Y., Inaka, K., Matsushima, M. and Kikuchi, M. (1992) Biochemistry 31, 7077–7085
37. Eijsink, V. G. H., Vriend, G., van de Burg, B., van de Zee, J. R., Veltman, O. R., Stulp, B. K. and Venema, G. (1993) Protein Engineer. 5, 157–163
38. Watanabe, K., Masuda, T., Ohashi, H., Mihara, H. and Suzuki, Y. (1994) Eur. J. Biochem. 226, 277–283
39. Watanabe, K., Chishiro, K., Kitamura, K. and Suzuki, Y. (1991) J. Biol. Chem. 266, 24287–24294
40. Hardy, F., Vriend, G., Veltman, Q. R., van de Vinne, B., Venema, G. and Eijsink, V. G. H. (1993) FEBS Lett. 317, 89–92
41. Tomazic, S. J. and Klibanov, A. M. (1988) J. Biol. Chem. 263, 3086–3091
42. Meng, M., Bagdasarian, M. and Zeikus, J. G. (1993) Biotechnology 11, 1157–1161
43. Ahern, T. J. and Klibanov, A. M. (1988) Meth. Biochem. Anal. 33, 91–127
44. Segel, I. H. (1975) in Enzyme kinetics: behavior and analysis of rapid equilibrium and steady-state enzyme systems, pp. 929–934, John Wiley & Sons, N.Y.
45. Londesborough, J. (1980) Eur. J. Biochem. 105, 211–215
46. Vieille, C., Hess, J. M., Kelly, R. M., and Zeikus, J. G. (1995) Appl. and Environ. Microbiol. 61, 1867–1875
47. Jencks, W. P. (1975) in Advances in enzymology and related areas of molecular biology, vol. 43, (Meister, A., ed.), pp. 219–411, John Wiley & sons, N.Y.

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1630 base pairs
      (B) TYPE: nucleic acid
      (C) STRANDEDNESS: double
      (D) TOPOLOGY: linear    (ii) MOLECULE TYPE: DNA (genomic)

(vi) ORIGINAL SOURCE:
      (A) ORGANISM: Thermophilic bacterium
      (B) STRAIN: Thermoanaerobacter ethanolicus 39E    (ix) FEATURE:
      (A) NAME/KEY: CDS
      (B) LOCATION: 238..1296
      (D) OTHER INFORMATION: /product= "secondary-alcohol
         dehydrogenase"

(ix) FEATURE:
      (A) NAME/KEY: CDS
      (B) LOCATION: 1496..1630

(xi) SEQUENCE DESCRIPTION: SEQ ID NO:1:

```
TGAACAATAG ACAACCCCTT TCTGTGATCT TGTTTTTTGC AAATGCTATT TTATCACAAG      60

AGATTTCTCT AGTTCTTTTT TACTTAAAAA AACCCTACGA AATTTTAAAC TATGTCGAAT     120

AAATTATTGA TAATTTTTAA CTATGTGCTA TTATATTATT GCAAAAAATT TAACAATCAT     180

CGCGTAAGCT AGTTTTCACA TTAATGACTT ACCCAGTATT TTAGGAGGTG TTTAATG       237

ATG AAA GGT TTT GCA ATG CTC AGT ATC GGT AAA GTT GGC TGG ATT GAG      285
Met Lys Gly Phe Ala Met Leu Ser Ile Gly Lys Val Gly Trp Ile Glu
 1               5                  10                  15

AAG GAA AAG CCT GCT CCT GGC CCA TTT GAT GCT ATT GTA AGA CCT CTA      333
Lys Glu Lys Pro Ala Pro Gly Pro Phe Asp Ala Ile Val Arg Pro Leu
             20                  25                  30

GCT GTG GCC CCT TGC ACT TCG GAC ATT CAT ACC GTT TTT GAA GGA GCC      381
Ala Val Ala Pro Cys Thr Ser Asp Ile His Thr Val Phe Glu Gly Ala
         35                  40                  45

ATT GGC GAA AGA CAT AAC ATG ATA CTC GGT CAC GAA GCT GTA GGT GAA      429
Ile Gly Glu Arg His Asn Met Ile Leu Gly His Glu Ala Val Gly Glu
     50                  55                  60

GTA GTT GAA GTA GGT AGT GAG GTA AAA GAT TTT AAA CCT GGT GAT CGC      477
Val Val Glu Val Gly Ser Glu Val Lys Asp Phe Lys Pro Gly Asp Arg
 65                  70                  75                  80
```

```
GTT GTT GTG CCA GCT ATT ACC CCT GAT TGG TGG ACC TCT GAA GTA CAA      525
Val Val Val Pro Ala Ile Thr Pro Asp Trp Trp Thr Ser Glu Val Gln
             85                  90                  95

AGA GGA TAT CAC CAG CAC TCC GGT GGA ATG CTG GCA GGC TGG AAA TTT      573
Arg Gly Tyr His Gln His Ser Gly Gly Met Leu Ala Gly Trp Lys Phe
            100                 105                 110

TCG AAT GTA AAA GAT GGT GTT TTT GGT GAA TTT TTT CAT GTG AAT GAT      621
Ser Asn Val Lys Asp Gly Val Phe Gly Glu Phe Phe His Val Asn Asp
        115                 120                 125

GCT GAT ATG AAT TTA GCA CAT CTG CCT AAA GAA ATT CCA TTG GAA GCT      669
Ala Asp Met Asn Leu Ala His Leu Pro Lys Glu Ile Pro Leu Glu Ala
        130                 135                 140

GCA GTT ATG ATT CCC GAT ATG ATG ACC ACT GGT TTT CAC GGA GCT GAA      717
Ala Val Met Ile Pro Asp Met Met Thr Thr Gly Phe His Gly Ala Glu
145                 150                 155                 160

CTG GCA GAT ATA GAA TTA GGT GCG ACG GTA GCA GTT TTG GGT ATT GGC      765
Leu Ala Asp Ile Glu Leu Gly Ala Thr Val Ala Val Leu Gly Ile Gly
                165                 170                 175

CCA GTA GGT CTT ATG GCA GTC GCT GGT GCC AAA TTG CGT GGA GCC GGA      813
Pro Val Gly Leu Met Ala Val Ala Gly Ala Lys Leu Arg Gly Ala Gly
            180                 185                 190

AGA ATT ATT GCC GTA GGC AGT AGA CCA GTT TGT GTA GAT GCT GCA AAA      861
Arg Ile Ile Ala Val Gly Ser Arg Pro Val Cys Val Asp Ala Ala Lys
            195                 200                 205

TAC TAT GGA GCT ACT GAT ATT GTA AAC TAT AAA GAT GGT CCT ATC GAA      909
Tyr Tyr Gly Ala Thr Asp Ile Val Asn Tyr Lys Asp Gly Pro Ile Glu
        210                 215                 220

AGT CAG ATT ATG AAT CTA ACT GAA GGC AAA GGT GTC GAT GCT GCC ATC      957
Ser Gln Ile Met Asn Leu Thr Glu Gly Lys Gly Val Asp Ala Ala Ile
225                 230                 235                 240

ATC GCT GGA GGA AAT GCT GAC ATT ATG GCT ACA GCA GTT AAG ATT GTT     1005
Ile Ala Gly Gly Asn Ala Asp Ile Met Ala Thr Ala Val Lys Ile Val
                245                 250                 255

AAA CCT GGT GGC ACC ATC GCT AAT GTA AAT TAT TTT GGC GAA GGA GAG     1053
Lys Pro Gly Gly Thr Ile Ala Asn Val Asn Tyr Phe Gly Glu Gly Glu
            260                 265                 270

GTT TTG CCT GTT CCT CGT CTT GAA TGG GGT TGC GGC ATG GCT CAT AAA     1101
Val Leu Pro Val Pro Arg Leu Glu Trp Gly Cys Gly Met Ala His Lys
            275                 280                 285

ACT ATA AAA GGC GGG CTA TGC CCC GGT GGA CGT CTA AGA ATG GAA AGA     1149
Thr Ile Lys Gly Gly Leu Cys Pro Gly Gly Arg Leu Arg Met Glu Arg
290                 295                 300

CTG ATT GAC CTT GTT TTT TAT AAG CCT GTC GAT CCT TCT AAG CTC GTC     1197
Leu Ile Asp Leu Val Phe Tyr Lys Pro Val Asp Pro Ser Lys Leu Val
305                 310                 315                 320

ACT CAC GTT TTC CAG GGA TTT GAC AAT ATT GAA AAA GCC TTT ATG TTG     1245
Thr His Val Phe Gln Gly Phe Asp Asn Ile Glu Lys Ala Phe Met Leu
                325                 330                 335

ATG AAA GAC AAA CCA AAA GAC CTA ATC AAA CCT GTT GTA ATA TTA GCA     1293
Met Lys Asp Lys Pro Lys Asp Leu Ile Lys Pro Val Val Ile Leu Ala
                340                 345                 350

TAA AAATGGGGAC TTAGTCCATT TTTATGCTAA TAAGGCTAAA TACACTGGTT          1346
 *

TTTTTATATG ACACATCGGC CAGTAAACTC TTGGTAAAAA ATAACAAAA AATAGTTATT    1406

TTCTTAACAT TTTTACGCCA TTAACACTTG ATAACATCAT CGAAGAAGTA AATAAACAAC   1466

TATTAAATAA AGAAGAAGG AGGATTATC ATG TTC AAA ATT TTA GAA AAA AGA      1519
                              Met Phe Lys Ile Leu Glu Lys Arg
                                1                   5

GAA TTG GCA CCT TCC ATC AAG TTG TTT GTA ATA GAG GCA CCA CTA GTA     1567
```

```
Glu Leu Ala Pro Ser Ile Lys Leu Phe Val Ile Glu Ala Pro Leu Val
     10              15                  20

GCC AAA AAA GCA AGG CCA GGC CAA TTC GTT ATG CTA AGG ATA AAA GAA        1615
Ala Lys Lys Ala Arg Pro Gly Gln Phe Val Met Leu Arg Ile Lys Glu
 25              30                  35                  40

GGA GGA GAA AGA ATT                                                   1630
Gly Gly Glu Arg Ile
             45
```

(2) INFORMATION FOR SEQ ID NO:2:

(i) SEQUENCE CHARACTERISTICS:
        (A) LENGTH: 352 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Lys Gly Phe Ala Met Leu Ser Ile Gly Lys Val Gly Trp Ile Glu
 1               5                  10                  15

Lys Glu Lys Pro Ala Pro Gly Pro Phe Asp Ala Ile Val Arg Pro Leu
             20                  25                  30

Ala Val Ala Pro Cys Thr Ser Asp Ile His Thr Val Phe Glu Gly Ala
         35                  40                  45

Ile Gly Glu Arg His Asn Met Ile Leu Gly His Glu Ala Val Gly Glu
 50                  55                  60

Val Val Glu Val Gly Ser Glu Val Lys Asp Phe Lys Pro Gly Asp Arg
 65                  70                  75                  80

Val Val Val Pro Ala Ile Thr Pro Asp Trp Trp Thr Ser Glu Val Gln
             85                  90                  95

Arg Gly Tyr His Gln His Ser Gly Gly Met Leu Ala Gly Trp Lys Phe
                 100                 105                 110

Ser Asn Val Lys Asp Gly Val Phe Gly Glu Phe Phe His Val Asn Asp
             115                 120                 125

Ala Asp Met Asn Leu Ala His Leu Pro Lys Glu Ile Pro Leu Glu Ala
         130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                 165                 170                 175

Pro Val Gly Leu Met Ala Val Ala Gly Ala Lys Leu Arg Gly Ala Gly
             180                 185                 190

Arg Ile Ile Ala Val Gly Ser Arg Pro Val Cys Val Asp Ala Ala Lys
         195                 200                 205

Tyr Tyr Gly Ala Thr Asp Ile Val Asn Tyr Lys Asp Gly Pro Ile Glu
     210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                 245                 250                 255

Lys Pro Gly Gly Thr Ile Ala Asn Val Asn Tyr Phe Gly Glu Gly Glu
             260                 265                 270

Val Leu Pro Val Pro Arg Leu Glu Trp Gly Cys Gly Met Ala His Lys
         275                 280                 285

Thr Ile Lys Gly Gly Leu Cys Pro Gly Gly Arg Leu Arg Met Glu Arg
     290                 295                 300
```

```
Leu Ile Asp Leu Val Phe Tyr Lys Pro Val Asp Pro Ser Lys Leu Val
305                 310                 315                 320

Thr His Val Phe Gln Gly Phe Asp Asn Ile Glu Lys Ala Phe Met Leu
                325                 330                 335

Met Lys Asp Lys Pro Lys Asp Leu Ile Lys Pro Val Val Ile Leu Ala
                340                 345                 350
```

(2) INFORMATION FOR SEQ ID NO:3:

(i) SEQUENCE CHARACTERISTICS:
        (A) LENGTH: 45 amino acids
        (B) TYPE: amino acid
        (D) TOPOLOGY: linear     (ii) MOLECULE TYPE: protein     (xi) SEQUENCE DESCRIPTION: SEQ ID NO:3:

```
Met Phe Lys Ile Leu Glu Lys Arg Glu Leu Ala Pro Ser Ile Lys Leu
1               5                   10                  15

Phe Val Ile Glu Ala Pro Leu Val Ala Lys Lys Ala Arg Pro Gly Gln
                20                  25                  30

Phe Val Met Leu Arg Ile Lys Glu Gly Gly Glu Arg Ile
                35                  40                  45
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:4:

ATGAARGGNT THGCNATGYT                                              20

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:5:

GWNGTCATCA TRTCNGKDAT CAT                                          23

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:6:

CGGGGTACCC CGTATTTTAG GAGGTGTTTA A                                  31

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:7:

CAGTCCGGGC CCTTATGCTA ATATTACAAC AGGTTTG        37

TABLE 1

Comparison of primary structural similarity between primary and secondary alcohol dehydrogenases % Identity (% similarity) of sequence with sequences from the following organisms:

| Organism | T. eth | T. bro | C. bei | A. eut | B. ste | S. sul | Z. mob | Liver |
|---|---|---|---|---|---|---|---|---|
| 2° Adh | | | | | | | | |
| T. eth | 1 | | | | | | | |
| T. bro | 99.1 (99.4) | 1 | | | | | | |
| C. bei | 74.4 (86.6) | 75.0 (86.9) | 1 | | | | | |
| A. eut | 35.6 (61.5) | 36.2 (62.1) | 36.2 (59.5) | 1 | | | | |
| 1° Adh | | | | | | | | |
| B. ste | 26.7 (50.6) | 27.2 (50.8) | 24.1 (50.6) | 31.9 (53.8) | 1 | | | |
| S. sul | 27.0 (51.6) | 26.4 (51.0) | 24.0 (50.6) | 25.8 (49.0) | 35.2 (55.8) | 1 | | |
| Z. mob | 24.2 (48.2) | 25.1 (48.8) | 20.5 (48.4) | 25.6 (51.2) | 54.0 (71.0) | 33.9 (54.6) | 1 | |
| Liver | 28.8 (53.8) | 29.1 (54.4) | 27.4 (52.6) | 23.1 (49.7) | 32.8 (55.4) | 28.9 (50.9) | 31.1 (50.4) | 1 |

T. eth: *Thermoanaerobacter ethanolicus* 39E;
T. bro: *Thermoanaerobacter brockii*;
C. bei: *Clostridium beijerinckii*;
A. eut: *Alcaligenes eutrophus*;
B. ste: *Bacillus stearothermophilus*;
S. sul: *Sulfalobus sulfataricus*;
Z. mob: *Zymomonas mobilis*.
Thermophilic Adh: *T. ethanolicus, T. brockii, B. stearothermophilus,* and *S. sulfataricus*.
mesophilic Adh: *C. beijerinckii, A. eutrophus, Z. mobilis,* horse liver.

We claim:

1. An isolated and purified nucleic acid molecule encoding a secondary alcohol dehydrogenase enzyme, the nucleic acid molecule comprising the sequence set forth in SEQ ID NO:1 between positions 238 and 1296.

2. A nucleic acid molecule as set forth in claim 1 comprising the sequence set forth in SEQ ID NO:1.

* * * * *